United States Patent [19]

Reed

[11] Patent Number: 4,477,779
[45] Date of Patent: Oct. 16, 1984

[54] DUAL CHANNEL GATED PEAK DETECTOR

[75] Inventor: Robert W. Reed, State College, Pa.

[73] Assignee: The United States of America as represented by the Secretary of the Navy, Washington, D.C.

[21] Appl. No.: 403,688

[22] Filed: Jul. 30, 1982

[51] Int. Cl.$^3$ .................. H03K 5/00; H03K 17/00; H03K 5/22

[52] U.S. Cl. ................................ 328/151; 328/117; 307/351; 364/481

[58] Field of Search ............... 328/150, 151, 115, 116, 328/117; 364/857, 481, 483; 307/350, 352; 330/279

[56] References Cited

U.S. PATENT DOCUMENTS

| | | | |
|---|---|---|---|
| 3,728,535 | 4/1973 | Dickman et al. | 364/481 |
| 3,733,553 | 5/1973 | Magnante et al. | 325/321 |
| 3,764,923 | 10/1973 | Woodworth et al. | 328/175 |
| 3,995,224 | 11/1976 | Sutphin, Jr. | 328/168 |
| 4,151,481 | 4/1979 | Funston et al. | 330/279 |
| 4,213,097 | 7/1980 | Chiu et al. | 330/51 |
| 4,219,839 | 8/1980 | Watanabe | 307/351 |
| 4,241,455 | 12/1980 | Eibner | 328/117 |
| 4,263,560 | 4/1982 | Ricker | 330/129 |
| 4,298,841 | 11/1982 | Dishal | 328/150 |

Primary Examiner—John S. Heyman
Assistant Examiner—Timothy P. Callahan
Attorney, Agent, or Firm—R. F. Beers; F. I. Gray

[57] ABSTRACT

A dual channel peak detector having an automatic gain control (AGC) circuit maintains an internal replica of a gated input signal waveform at a constant peak level. An rf signal is input to a double balanced mixer to select that portion of the signal within the time interval of interest. A delay and gate generator circuit provides a variable delay from a sync input and generates a variable length gate which gates on the double balance mixer to pass the signal of interest to the remainder of the peak detector circuit. The gated signal is amplified and multiplied by a pseudo dc signal from the AGC circuit. The peak level of the resultant gated signal is detected. The detected peak level is sampled and input to the AGC circuit which computes the AGC circuit output voltage required to maintain a constant detected peak level amplitude. The AGC circuit output voltage is summed with the voltage from a second channel, and is also output as a dB value and a ratio between channels.

6 Claims, 10 Drawing Figures

DUAL CHANNEL GATED PEAK DETECTOR

BACKGROUND OF THE INVENTION

1. Field of the Invention

The present invention relates to electrical circuits, and more particularly to a dual channel gated peak detector.

2. Description of the Prior Art

In the fabrication of plate stock one of the steps involves the production of a metal matrix precursor wire by a liquid metal state infiltration process on a graphite fiber. It is desired to acoustically inspect the precursor wire immediately following liquid aluminum infiltration to ascertain its quality in terms of completeness of penetration of the metal into the fiber tow. A "sending" transducer transmits an ultrasonic signal into the wire, which signal is picked up by two spaced apart receivers. The relative amplitude of the two pulses as well as the time delay are critical factors in the inspection process. Currently, oscilloscopes and/or X-Y recorders are used to determine these amplitude and time delay parameters.

SUMMARY OF THE INVENTION

Accordingly, the present invention provides a dual channel peak detector having an automatic gain control (AGC) circuit to maintain an internal replica of a gated input signal waveform at a constant peak level. An rf signal is input to a double balanced mixer to select that portion of the signal within the time interval of interest. A delay and gate generator circuit provides a variable delay from a sync input and generates a variable length gate which gates on the double balance mixer to pass the signal of interest to the remainder of the peak detector circuit. The gated signal is amplified and multiplied by a pseudo dc signal from the AGC circuit. The peak level of the resultant gated signal is detected. The detected peak level is sampled and input to the AGC circuit which computes the AGC circuit output voltage required to maintain a constant detected peak level amplitude. The AGC circuit output voltage is summed with the same voltage from a second channel, and is also output as a dB value and a dB ratio between channels.

Therefore it is an object of the present invention to provide a dual channel peak detector for determining the dB of the relative amplitude between two signals.

Another object of the present invention is to provide a "phase" stable trigger signal for measuring the time delay between signals of similar waveforms appearing within the gate time interval in each channel.

Other objects, advantages and novel features of the present invention will be apparent from the following detailed description when read in conjunction with the appended claims and attached drawing.

DESCRIPTION OF THE PREFERRED EMBODIMENT

Figure 1:
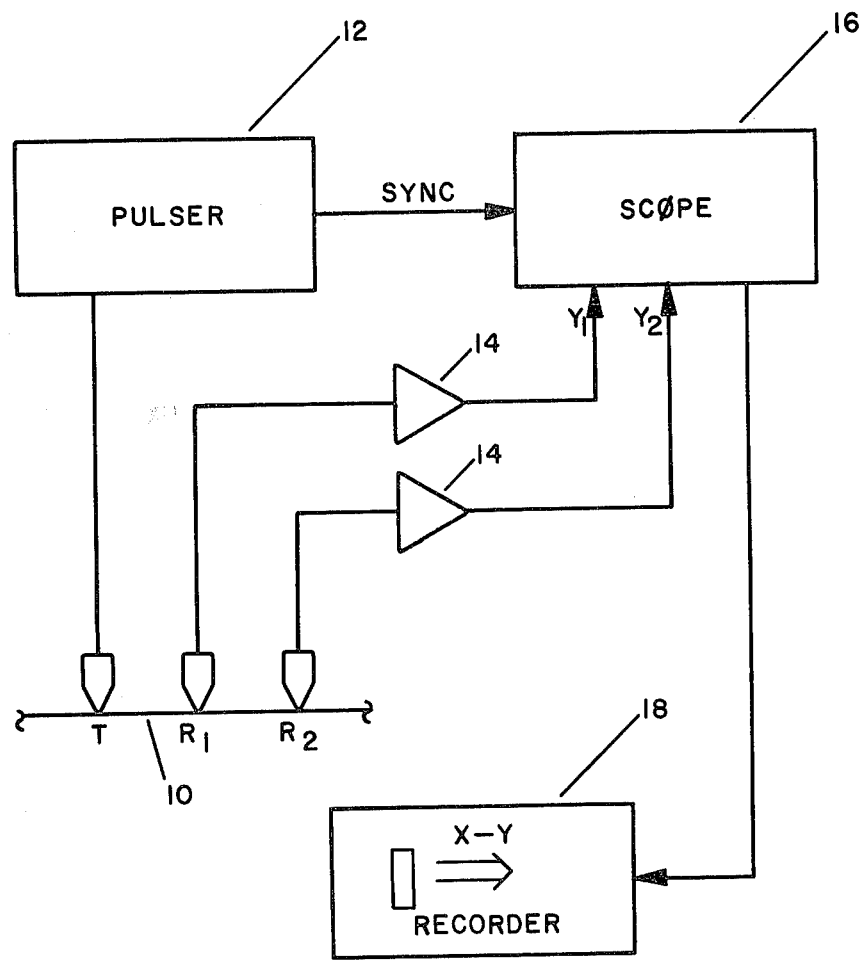
FIG. 1 is a block diagram for a typical prior art wire inspection system.

Referring to FIG. 1 a wire 10, which is being inspected after a metal infiltration process, passes by a transmitting transducer, T, and two spaced apart receiver transducers, $R_1$ and $R_2$. A pulser 12 excites the transmitter T with an ultrasonic pulse which is induced into the wire 10. The ultrasonic pulse travels along the wire 10 where it is detected by receivers $R_1$ and $R_2$ at times $t_1$ and $t_2$, respectively. Amplifiers 14 amplify and buffer the signals from the receivers $R_1$ and $R_2$. The signals are displayed on an oscilloscope 16 which is synced by the pulser 12. The signals also may be displayed on an X-Y recorder 18 for a permanent record. From the displays the differential amplitude and time delay, $t_2-t_1$, may be crudely determined.

Figure 2:
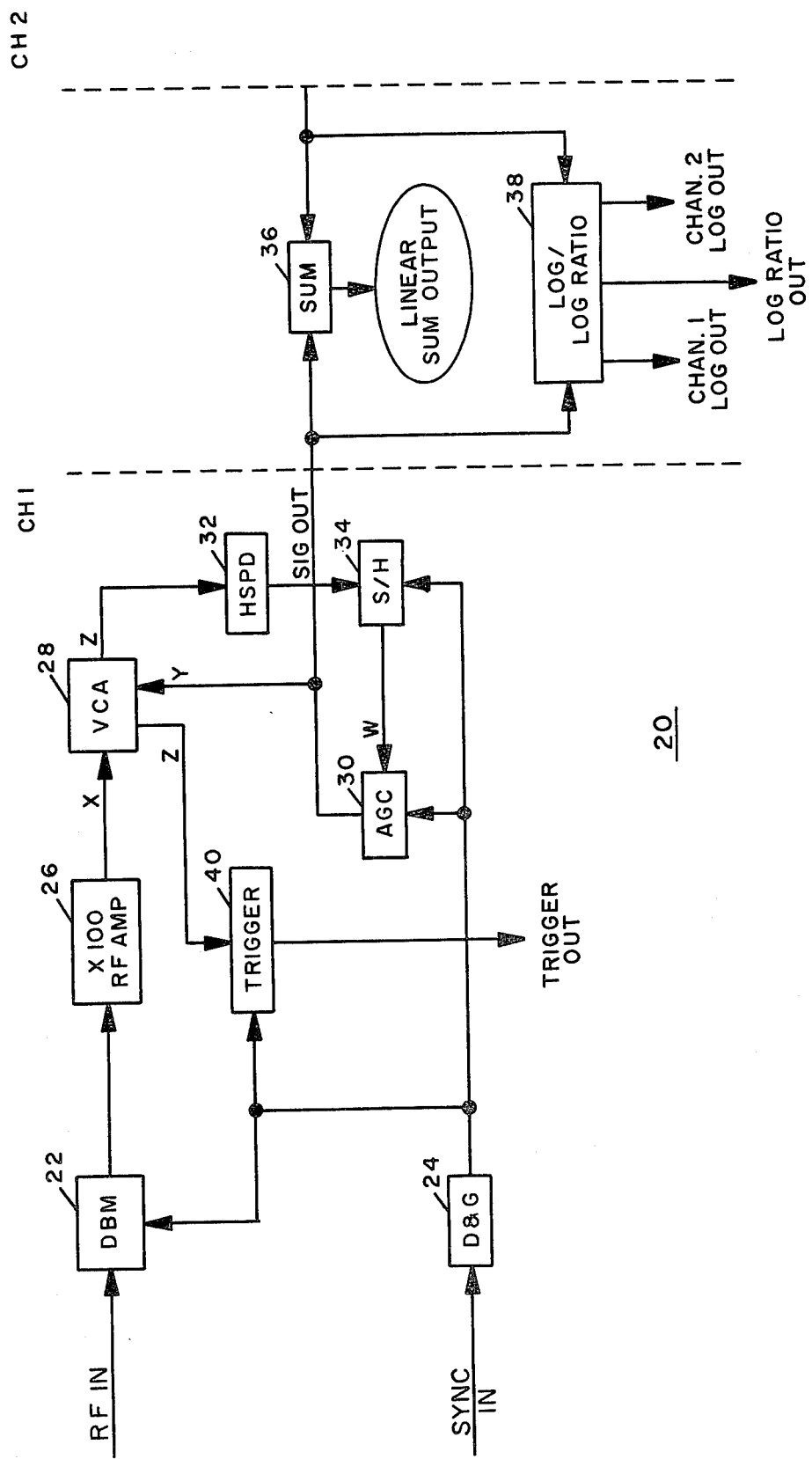
FIG. 2 is a functional block diagram for a dual-channel gated peak detector according to the present invention.

A dual channel gated peak detector 20 as shown in FIG. 2 replaces the oscilloscope 16 of FIG. 1 for determining the relative amplitudes of the received signals and for determining the time difference between $t_1$ and $t_2$. Since the two channels, CH1 and CH2, are identical, only one channel is discussed in detail here. The rf signal from one of the receivers, $R_1$ or $R_2$, the peak value of which is to be detected, is input to a double balanced mixer (DBM) 22. A delay and gate (D & G) 24 gates on the DBM 22 to select only that portion of the signal in the time interval of interest. The D&G 24 is set to provide a variable width gate signal to the DBM 22 at a variable time delay after the sync signal input. The gated rf signal from the DBM 22 is amplified by an rf amplifer 26 before it enters a voltage controlled amplifer (VCA) 28 which is a high-speed analog multiplier circuit. The output of the VCA 28 is the weighted product, Z, of its two inputs: X, the gated rf signal of interest, and Y, a dc output voltage from an automatic gain control (AGC) circuit 30. A high speed peak detector (HSPD) 32 detects the peak value of output of the VCA 28. The peak value is stored in a sample and hold (S/H) circuit 34. The AGC circuit 30 compares the weighted peak value of Z from the S/H circuit 34 with an internal reference voltage and adjusts its output Y to maintain the peak value of Z equal to the internal reference voltage. A sum circuit 36 takes the sum of the AGC output level voltages, Y, of the two channels, CH1 and CH2. A log/log ratio circuit 38 computes the logarithm of the AGC output levels, Y, of both channels, and subtracts the two logarithmic voltages to yield a log ratio output. A trigger circuit 40 also receives the amplitude controlled gated rf signal from the VCA 28, Z, and the gate pulse from the D&G circuit 24 to generate a timing pulse located at a fixed phase position on the gated, gain controlled rf signal, Z, from the VCA.

Figure 3:
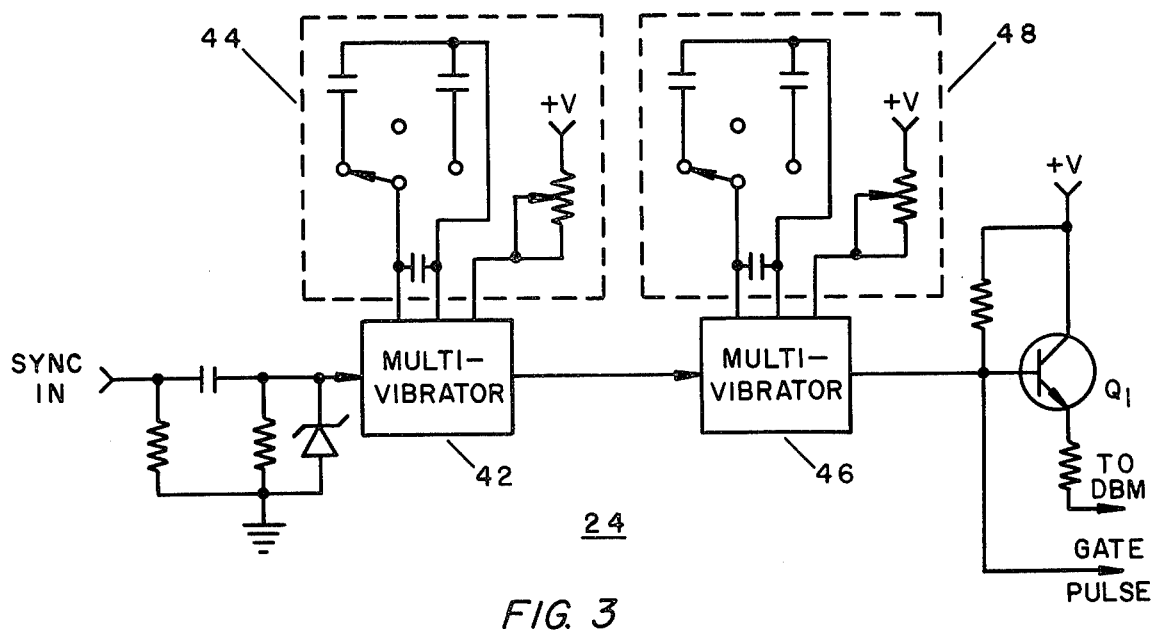
FIG. 3 is a schematic diagram for the delay and gate generator circuit of FIG. 2.

FIG. 3 is a schematic diagram for the delay and gate generator 24. The sync signal input is a positive fast pulse. A first monostable multivibrator 42, triggered by the sync signal input, has a delay control 44 to provide a variable delay output pulse whose width is determined by the setting of the delay control. The trailing edge of the delay output pulse triggers a second monostable multivibrator 46 to generate a gate pulse. A gate control 48 sets the output gate width from the second multivibrator 46. A transistor $Q_1$ converts the gate pulse into a current drive signal used to drive the DBM 22 signal gate.

Figure 4:
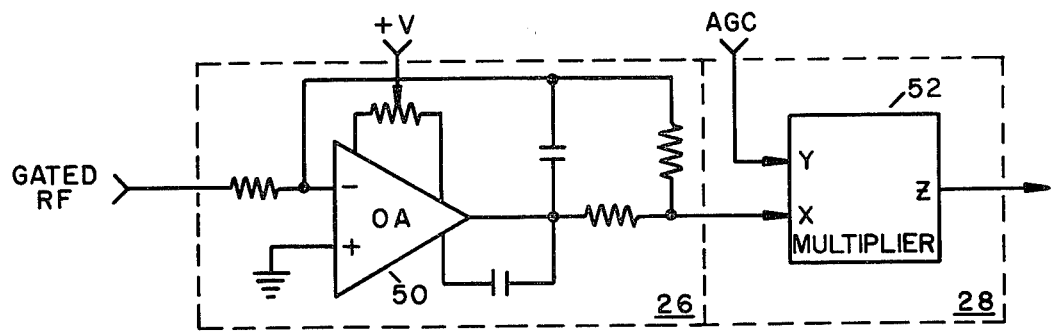
FIG. 4 is a schematic diagram for the rf amplifier and voltage controlled amplifier circuits of FIG. 2.

The rf amplifier 26, as shown in FIG. 4, is a high gain (40 dB) wideband operational amplifier 50. The input of the OP AMP 50 is impedance matched to the output of the DBM 22. Since the DBM 22 clips at a low level, the OP AMP 50 provides the output level required by the following circuitry while permitting the DBM to operate at signal levels below its clipping point. The VCA 28 is a four quadrant multiplier 52. The four quadrant capability of the multiplier 52 permits the VCA 28 to invert an incoming rf signal, X, by simply changing the sign of the Y channel input which is typically a pseudo dc signal from the AGC circuit 30. In this way the peak detector 32 and AGC 30 circuits, which are sensitive in this embodiment only to positive input signal voltages, can be used on the negative portions of the rf signal by inverting the Y signal which in turn inverts the signal output, Z. The functional form of the multiplier circuit 52 is $Z = X \cdot Y/k$ where k is a constant weight factor of the circuit such as $k = 10$.

Figure 5:
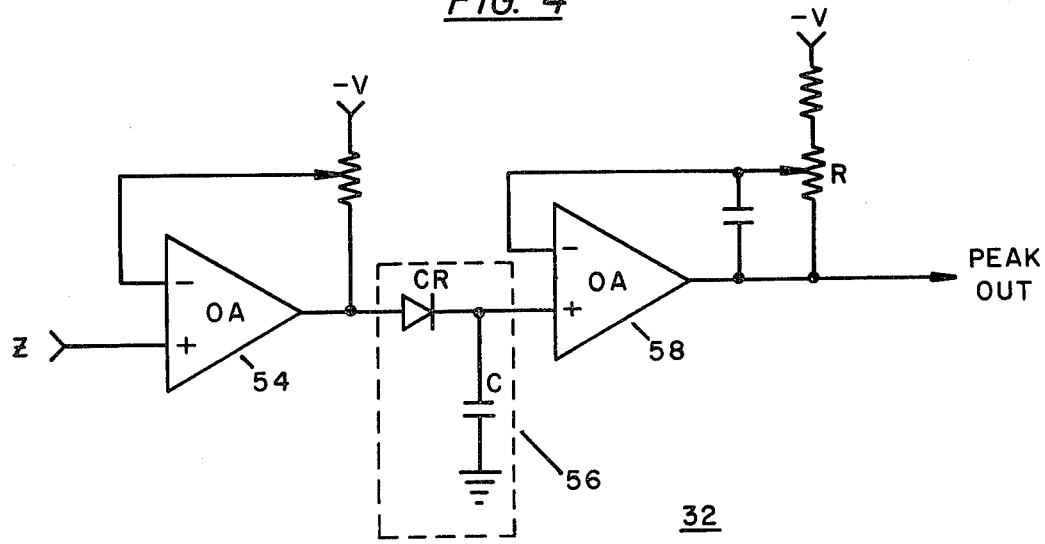
FIG. 5 is a schematic diagram for the high speed peak detector circuit of FIG. 2.

The HSPD circuit 32 of FIG. 5 uses two fast operational amplifiers to find the peak level of Z from the VCA 28. A first OP AMP 54 has a precise gain k that compensates for the division built into the transfer function of the multiplier 50. A peak detector 56, having a diode CR and a capacitor C, has a high charging rate due to the low output impedance of the first OP AMP 54. A second OP AMP 58 provides a very high input impedance for minimizing the decay rate of the peak detected voltage stored on C. A dc bias offset capability is provided in the second OP AMP 58 and is adjusted by resistor R. The decay time for the peak detecting circuit 32 is set for the signal to fall to 1/e of the peak-detected value. The decay rate is faster than or equal to the maximum expected for signal level changes on a pulse-to-pulse basis to enable the following circuitry to follow signals both increasing and decreasing with time without excessive lags. For a given application the decay time is 1.5 msec with the decay ratio permitting repetition rates in excess of 5 kHz with a minimum sample time of 4 $\mu$sec. The output of the HSPD circuit 32 is then a positive voltage equal to the peak of either the positive or negative half of the gated rf input signal from the VCA 28.

Figure 6:
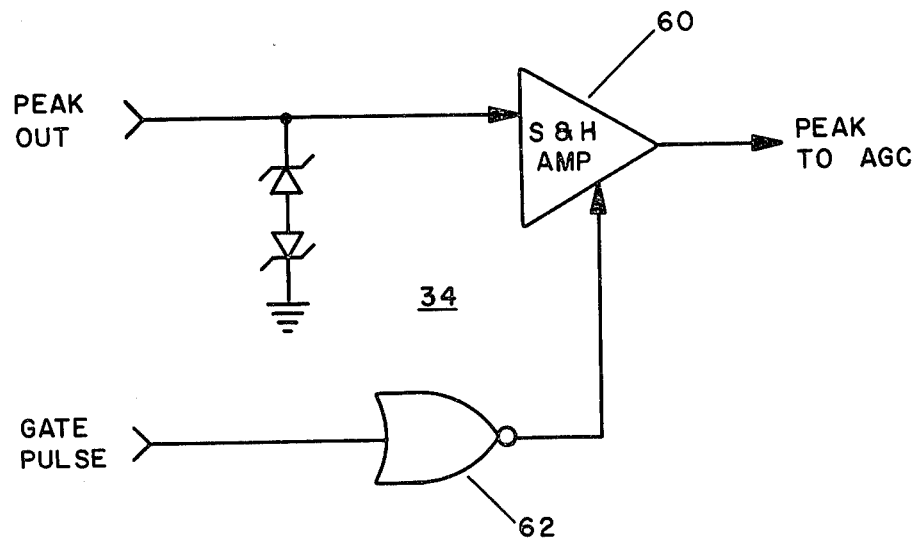
FIG. 6 is a schematic diagram for the sample and hold circuit of FIG. 2.

The S&H circuit 34 of FIG. 6 has an amplifier 60 which is gated on by the gate pulse which is inverted by a NOR gate 62. The peak level out from the amplifier 60 is input to the AGC circuit 30.

Figure 7:
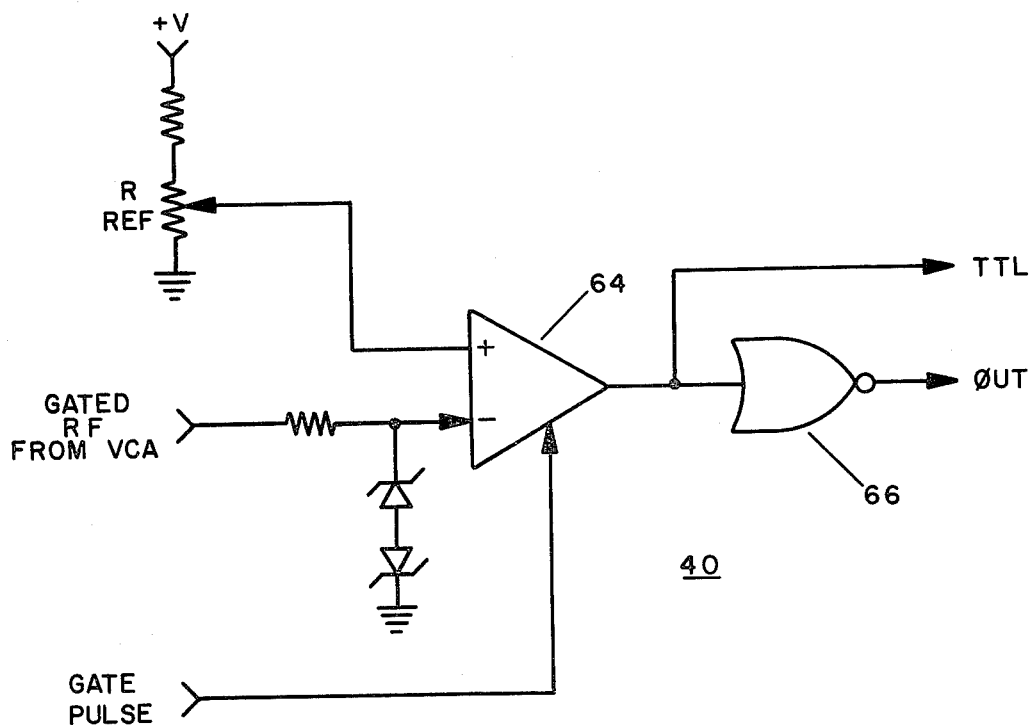
FIG. 7 is a schematic diagram for the trigger circuit of FIG. 2.

The trigger circuit 40 of FIG. 7 has a high speed gateable comparator 64 which functions as a comparator during the time interval it is enabled by the gate pulse. The comparator 64 compares the level of gated rf signal from the VCA 28 with a fixed reference voltage level determined by the setting of resistor $R_{REF}$. When the input signal voltage exceeds the reference voltage, the comparator output, TTL OUT switches states (+V to zero). Since the purpose of the AGC circuit 30 is to maintain the gated rf output from the VCA 28 at a fixed peak level for the gated portion of the signal, the input to the comparator 64 is always at a fixed peak level, except for circuit noise. Hence the comparator 64 always switches states on repetitive signals at the same phase position on the waveform and provides a time, t. The reference level set by $R_{REF}$ is typically set about halfway between the peak level of the signal from the VCA 28 and the noise level to minimize the noise impact on the signal timing and to maintain good sensitivity. The output of the comparator is available also as a buffered and inverted output from a second NOR gate 66. To compute the time delay between the two channels, the time t from each channel may be input to a commercially available digital, dual-channel, time interval counter. The maintenance of the constant voltage level signal permits very accurate time delay determination between similar signals appearing within the gate time windows of each channel. The number of channels may be conveniently expanded to provide for additional signal processing.

Figure 8:
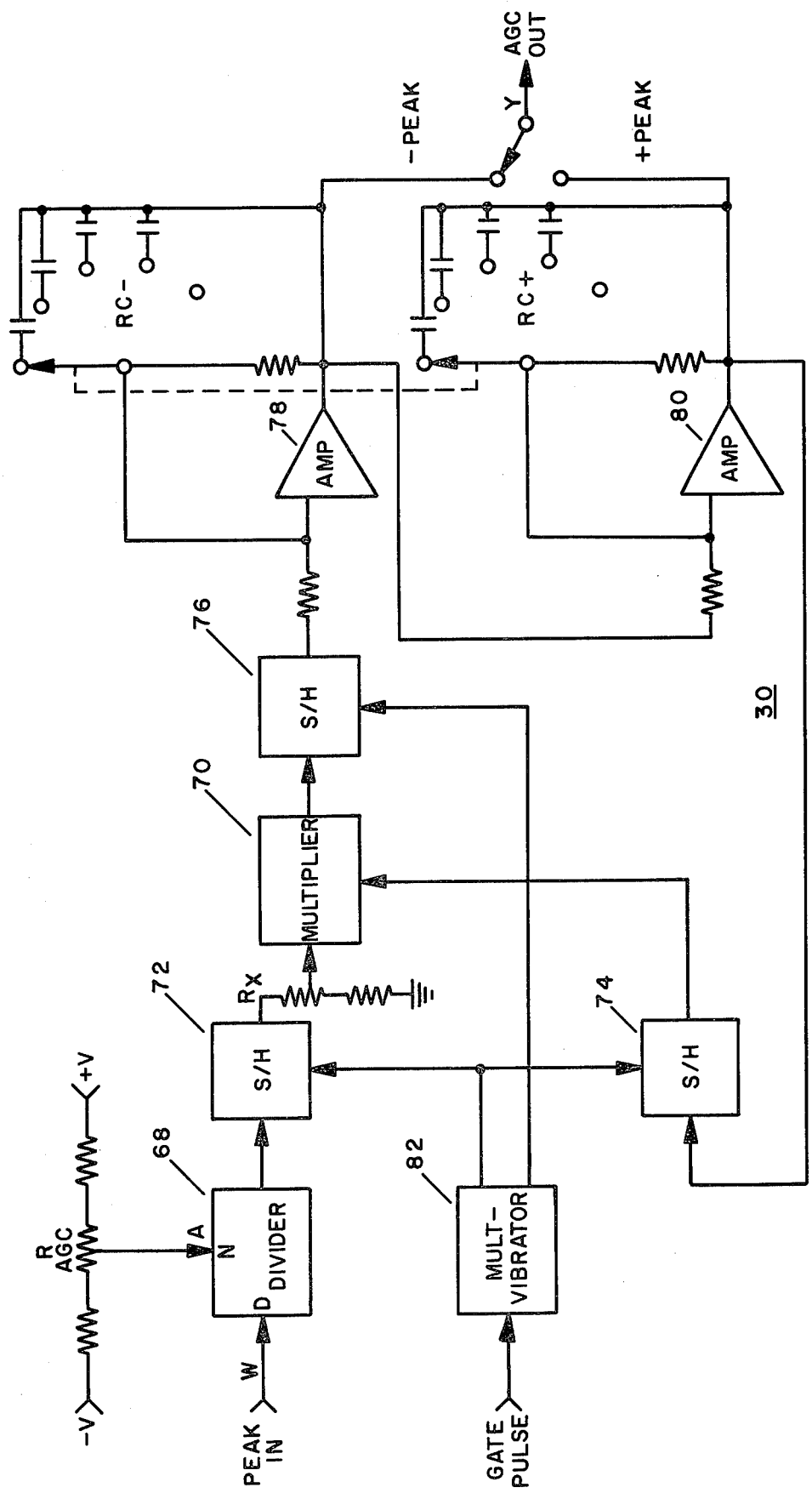
FIG. 8 is a schematic diagram for the automatic gain control circuit of FIG. 2.

The AGC circuit 30, shown schematically in FIG. 8 uses an accurate analog divider 68 and a multiplier 70 together with a number of sample and hold (S/H) circuits 72, 74, 76 to compute the AGC output voltage required for driving the VCA 28 to yield a peak level voltage from the HSPD circuit 32 which is constant in amplitude. The computations are made on a cycle by cycle basis with the result that after each cycle the AGC OUT is such that if the next cycle has an input signal identical to the present cycle, no change is required in AGC OUT. Hence, AGC OUT always is lagging the input by one cycle, i.e., AGC OUT is that signal which would have caused the peak value of the previous input signal to be coincident with the AGC internal reference level.

Operationally the AGC circuit 30 behavior is intimately tied to the previously described circuits, particularly the VCA 28, the HSPD circuit 32 and the S/H circuit 34. The VCA 28 inputs are the gated rf signal, X, and the gain control signal, Y, generated by the AGC circuit 30. The output of the VCA 28 is $X \cdot Y/k = Z$. The HSPD circuit 32 and S/H circuit 34 provide a multiplication factor of k, so the input to the AGC circuit 30 is $W = kZ = X \cdot Y$.

The AGC circuit 30 adjusts Y to maintain W at a fixed value. To fully describe circuit operation two sync cycles, t and t+1, are considered. The divider circuit 68 has as a numerator input the AGC reference level, A, which is determined by a potentionmeter $R_{AGC}$. The denominator input is W. The output of the divider circuit 68 is $(A/W) \cdot k$, or $(A/W_t) \cdot k$ for cycle t. This level is stored in the first S/H circuit 72 between cycles and is input to the multiplier 70. The other multiplicand is $Y_t$ which was stored from cycle $t-1$ by the second S/H circuit 74. The transfer function of the multiplier 70 involves a division by k. Therefore, the output of the multiplier 70 is $$Y_{t+1} = [(A/W_t) \cdot k] \cdot [Y_t/k] = A \cdot Y_t/W_t.$$

This result is labeled $Y_{t+1}$ since this value is stored in the third S/H circuit 76 for use as Y during the cycle t+1. This voltage $Y_{t+1}$ is stored by the third S/H circuit 76 during the circuit gate interval so that the Y input to the VCA 28 is constant for the gate time interval. A pair of OP AMPS 78, 80 have a variable circuit time constant, RC− and RC+, respectively, for smoothing AGC OUT, and for providing a negative value of Y as is required to permit the VCA 28 to invert the input signal when desired. If $W_{t+1} = A$, then $Y_{t+}$ $1 = Y_{t'}$. At time $t'$ let there be a step change in the peak level of the gated rf signal, so that for $t < t'$ the level is a fixed constant value and for $t \geq t'$ a new fixed level exists which leads to $W_{t'} < A$. The AGC circuit 30 for this $t'$ cycle changes $Y_{t'+1}$ by exactly the correct amount to cause $W_{t'+1} = A$ and $Y_{t'+1}$ to equal the $Y_t'$ value that would have resulted in $W_t' = A$. A monostable multivibrator 82 provides from the GATE PULSE the necessary sample and hold timing signals for the S/H circuits 72, 74, 76.

Since the Y output of the AGC circuit 30 is the signal output, the value of Y is proportional to 1/X where X is the peak voltage of the rf input waveform. Thus, the log of Y gives dB changes that correspond directly to dB changes in the attenuation of X. Furthermore, an *increase* in the attenuation of X leads to an increase in the numerical value of the log output rather than a decrease as is typically the case in more conventional gated peak detectors.

Figure 9:
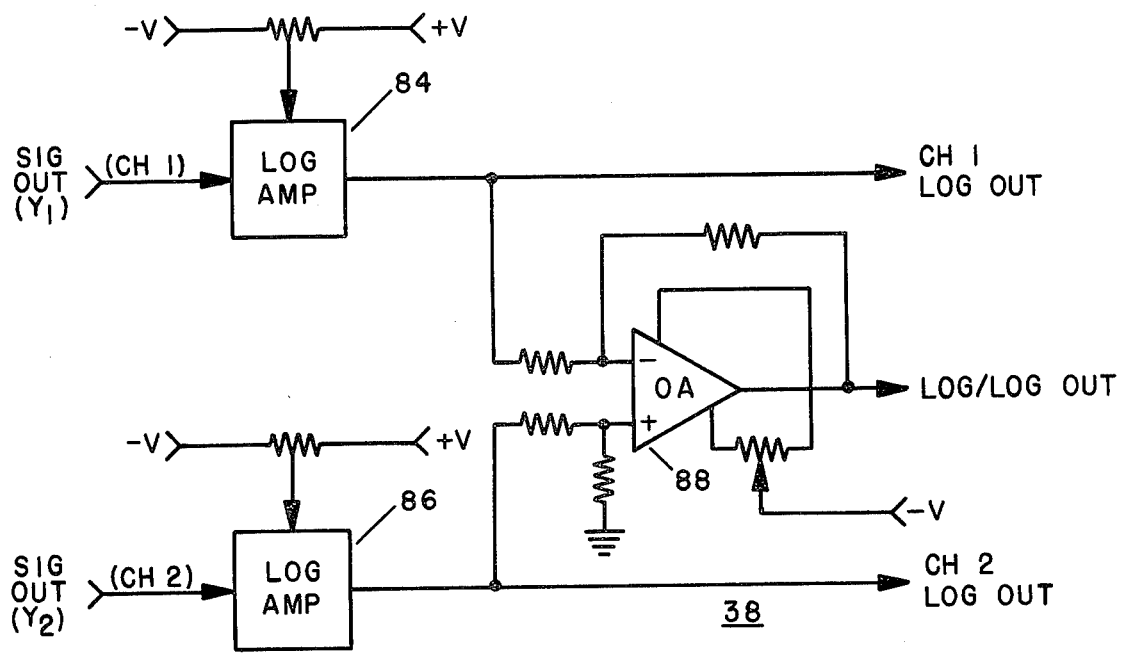
FIG. 9 is a schematic diagram for the log/log ratio circuit of FIG. 2.

The log/log ratio circuit 38, shown in FIG. 9, uses two log amplifier modules 84, 86 to compute the logarithm of the AGC voltage levels, $Y_1$ and $Y_2$, of both channels. The two outputs of the two log amplifiers 84, 86 are subtracted by an operational amplifier 88 to yield a log ratio output. The outputs may be scaled to give 0.1V/dB.

Figure 10:
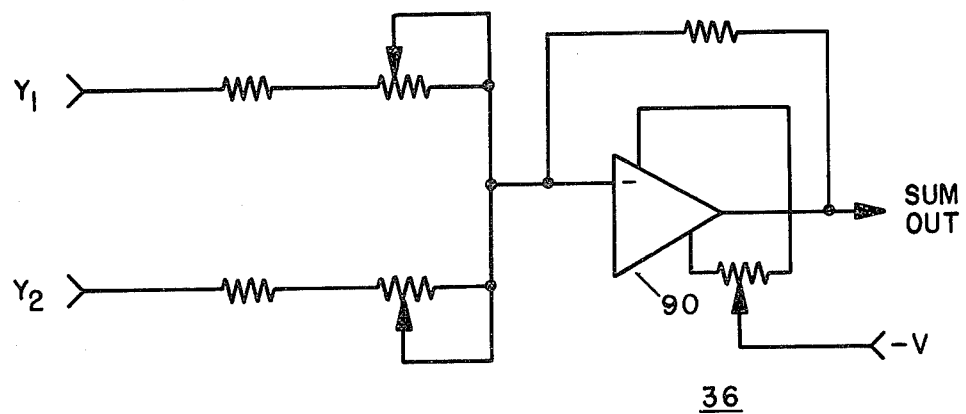
FIG. 10 is a schematic diagram for the sum circuit of FIG. 2.

The sum circuit 36, shown in FIG. 10, sums the AGC voltage level outputs, $Y_1 + Y_2$, of the two channels. A summing OP AMP 90 with a gain of ½ provides an output that remains within range for summing two full scale input signals. If the same rf input signal is applied to both channels and one channel is set for the + peak value and the other for the − peak value, a peak-to-peak signal results at SUM OUT.

Thus, the present invention provides a dual channel gated peak detector for determining the attenuation in signal between two spaced apart receivers of a transmitted ultrasonic pulse, and for determining the time at which the signal is received at each receiver from which the time delay is determined.

What is claimed is:

1. A dual channel gated peak detector comprising: two signal channels, each of said signal channels having:
   means for generating a gated signal from an input signal;
   means for combining said gated signal with a gain control voltage to produce a constant peak level signal;
   means for detecting said constant peak level signal to provide a peak level voltage; and
   means for computing said gain control voltage for each cycle of said peak level signal such that said peak level voltage is constant in amplitude.
   means for summing said gain control voltages from each of said signal channels to provide an output voltage inversely proportional to the amplitudes of said input signals to each of said signal channels.

2. A dual channel gated peak detector as recited in claim 1 wherein each of said signal channels further comprises means for generating a trigger pulse for each cycle of said peak level signal such that said trigger pulse occurs at the same phase position for each cycle of said constant peak level signal.

3. A dual channel gated peak detector as recited in claim 1 further comprising means for calculating the logarithm of said gain control voltage for each of said signal channels, and for calculating the logarithmic ratio between said gain control voltages from each of said signal channels.

4. A dual channel gated peak detector as recited in claims 1, 2, or 3 wherein said computing means comprises:
   means for dividing a gain reference voltage by said peak level voltage to provide a dividend voltage;
   means for multiplying said dividend voltage by said gain control voltage from the immediately preceding cycle of said gated signal to produce said gain control voltage for the current cycle; and
   means for storing said gain control voltage for one cycle.

5. A gated peak detector comprising:
   means for generating a gated signal from an input signal;
   means for combining said gated signal with a gain control voltage to produce a constant peak level signal;
   means for detecting said constant peak level signal to provide a peak level voltage; and
   means for computing said gain control voltage for each cycle of said peak level signal such that said peak level voltage is constant in amplitude.

6. A gated peak detector as recited in claim 5 further comprising means for generating a trigger pulse for each cycle of said constant peak level signal such that said trigger pulse occurs at the same phase position for each cycle of said constant peak level signal.

* * * * *